(12) United States Patent
Arndt et al.

(10) Patent No.: US 7,279,692 B2
(45) Date of Patent: Oct. 9, 2007

(54) MICROMECHANICAL INFRARED SOURCE

(75) Inventors: Michael Arndt, Reutlingen (DE); Gerd Lorenz, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 479 days.

(21) Appl. No.: 10/996,285

(22) Filed: Nov. 22, 2004

(65) Prior Publication Data

US 2005/0121630 A1 Jun. 9, 2005

(30) Foreign Application Priority Data

Dec. 3, 2003 (DE) ................. 103 56 508

(51) Int. Cl.
- *G01N 21/61* (2006.01)
- *H01K 5/02* (2006.01)
- *G01J 4/00* (2006.01)

(52) U.S. Cl. ............... 250/504 R; 250/495.1; 250/493.1; 219/543; 219/553; 338/308

(58) Field of Classification Search ............ 250/504 R
See application file for complete search history.

(56) References Cited

U.S. PATENT DOCUMENTS

| | | | | |
|---|---|---|---|---|
| 4,103,174 A | * | 7/1978 | McClatchie et al. | 250/493.1 |
| 4,378,489 A | * | 3/1983 | Chabinsky et al. | 219/543 |
| 4,644,141 A | * | 2/1987 | Hagen et al. | 219/543 |
| 5,350,927 A | * | 9/1994 | Rakhimov et al. | 250/504 R |
| 5,406,090 A | * | 4/1995 | Mattson et al. | 250/504 R |
| 5,472,720 A | * | 12/1995 | Rakhimov et al. | 426/241 |
| 5,576,553 A | * | 11/1996 | Adachi | 250/495.1 |
| 5,731,594 A | * | 3/1998 | Kuroda et al. | 250/504 R |
| 5,783,805 A | * | 7/1998 | Katzmann | 219/494 |
| 5,864,144 A | * | 1/1999 | Laine | 250/504 R |
| 5,910,659 A | * | 6/1999 | Johnson et al. | 250/495.1 |
| 6,049,080 A | * | 4/2000 | Ito | 250/338.3 |
| 6,646,233 B2 | * | 11/2003 | Kanno et al. | 219/390 |
| 6,805,946 B2 | * | 10/2004 | Mulligan et al. | 428/292.4 |
| 6,833,553 B2 | * | 12/2004 | Slingo | 250/504 R |
| 6,871,999 B2 | * | 3/2005 | Schieferdecker et al. | 374/128 |
| 6,921,910 B2 | * | 7/2005 | Curbelo | 250/504 R |
| 7,119,337 B1 | * | 10/2006 | Johnson et al. | 250/339.13 |
| 7,122,815 B2 | * | 10/2006 | Wood | 250/504 R |
| 2004/0254472 A1 | * | 12/2004 | McQuilkin | 600/473 |
| 2005/0051670 A1 | * | 3/2005 | Geyer et al. | 244/158 R |
| 2005/0121630 A1 | * | 6/2005 | Arndt et al. | 250/504 R |
| 2006/0226378 A1 | * | 10/2006 | Yabiku | 250/504 R |
| 2007/0057187 A1 | * | 3/2007 | Krummel et al. | 250/338.1 |

FOREIGN PATENT DOCUMENTS

| DE | 44 37 692 | 4/1996 |
|---|---|---|
| DE | 198 12 188 | 9/1999 |

\* cited by examiner

*Primary Examiner*—Robert Kim
*Assistant Examiner*—Bernard Souw
(74) *Attorney, Agent, or Firm*—Kenyon & Kenyon LLP

(57) ABSTRACT

A device for generating infrared radiation includes at least one heating element and at least one radiating element for irradiating the infrared radiation. The heating element is a micromechanical, two-dimensional heater structure. The heating element may be applied on the radiating element using hybrid technology such that the radiation element has at least one side facing the heating element and at least one side facing away. The radiating element may be ceramic substrate.

15 Claims, 2 Drawing Sheets

MICROMECHANICAL INFRARED SOURCE

FIELD OF THE INVENTION

The present invention relates generally to the infrared detection devices and more specifically to the detection of a gas or fluid using a micromechanical infrared sensor.

BACKGROUND INFORMATION

A spectroscopic measurement is used as a long-term stable and reproducible measuring principle in, for example, carbon dioxide sensors. The radiation of an infrared source in the MIR (mean infrared range) on a typical $CO_2$ absorption wavelength (e.g., 4.3 μm) is compared with the radiation of the infrared source for a reference wavelength (e.g., 4 μm). Information on whether and in what concentration $CO_2$ is present in the absorption path between the radiation source and the detector results from the comparison of the radiation intensity for the absorption wavelength and the reference wavelength.

Because of economic reasons, incandescent lamps, the irradiation spectrum of which reaches into the MIR range, are frequently used as the radiation source. The main limitation for the usability of the lamps is the MIR absorption of the lamp glass which limits the utilization of the incandescent lamps to the IR wavelength range<4.5 μm. Special glass qualities also absorb a large portion of the IR radiation in the wavelength range of just 4 μm. Due to the irradiation maximum of the incandescent filament of the lamp in the range of visible light (wavelength<1 μm), the largest portion of the generated radiation additionally represents a power loss which may also have a detrimental effect on the measuring accuracy.

Ceramic infrared radiators, special incandescent lamps made of silica glass, or devices known in the laboratory field as black-body radiators may represent alternatives to an incandescent lamp as an infrared source. If one intends to detect other gases, such as CO for example (absorption at 4.6 μm), using the above-mentioned spectroscopic measuring principle, one has to resort to these IR sources which are much more expensive and more complex.

An electrically operable tubular infrared radiator which is situated in a reflector is described in German Patent document No. 198 12 188. The ceramic infrared radiator has a carrier tube made of sintered $Al_2O_3$ and a heater coil made of resistor wire which is wound on the carrier tube, the resistor wire being enclosed and held by a cover layer made of a ceramic compound which, at least on its surface, is dyed black. The reflector is designed as a molded body made of ceramic material having a focal line, the reflector being gold-plated on its side facing the carrier tube including the heater coil. The carrier tube including the heater coil is situated in the area of the reflector's focal line.

A carbon dioxide sensor having a substrate carrier with a heating element including power terminals attached to its bottom side is described in detail in German Patent document No. 44 37 692. Interdigital electrodes with a carbon dioxide-sensitive material on top are situated on the top side.

SUMMARY OF THE INVENTION

The present invention relates to a device for generating infrared radiation, including at least one heating element and at least one radiating element for irradiating the infrared radiation. The heating element is a micromechanical, two-dimensional heater structure. This is a compact infrared radiator of small overall size and light weight, for specific applications, such as in the automotive field.

An example embodiment of the present invention provides that the heating element is applied on the radiating element using hybrid technology, the radiating element having at least one side facing the heating element and at least one side facing away from the heating element. Hybrid technology makes a particularly small overall size possible.

An example embodiment of the present invention provides that the radiating element is a ceramic substrate. Ceramic materials are characterized by a particularly high emissivity factor.

An example embodiment of the present invention provides that the ceramic is an aluminum oxide ceramic.

An example embodiment of the present invention provides that the side of the ceramic substrate facing away from the heating element is blackened, or is coated with a material that emits infrared radiation particularly well. A further increase in emissivity is thereby achieved.

An example embodiment of the present invention provides that ruthenium oxide is the material that emits infrared radiation particularly well.

An example embodiment of the present invention provides that the heater structure is made of platinum. Platinum is suited for the long-term stable generation of high temperatures and does not readily oxidize.

An example embodiment of the present invention provides that the heating element has at least one side facing away from the radiating element, and the side facing away from the radiating element is polished. The intensity of the infrared radiation emitted toward the side facing away from the radiating element is thereby further reduced.

An example embodiment of the present invention provides that the device is designed as a micromechanical element, the bottom side of the heating element being directly or indirectly applied on a diaphragm, and the top side of the heating element being directly or indirectly coated with an emission layer. The irradiations on the bottom side of the heating element are reduced due to the application above the diaphragm. The term "indirect" is to be understood as layers that are by all means not essential to the present invention but are required technologically such as, for example, a protective layer or an adhesion-enhancing layer, and that may be situated between the heating element and the diaphragm, and/or between the heating element and the emission layer, for exemplary purposes only.

An example embodiment of the present invention provides that the emission layer is made of ruthenium oxide.

An example embodiment of the present invention provides that there is a hollow space below the side of the diaphragm facing away from the heating element. A reduction in the irradiation toward this side is thereby achieved.

An example embodiment of the present invention provides that the diaphragm is designed using micromechanical silicon technology.

An example embodiment of the present invention provides that the device is used for analyzing gases.

An example embodiment of the present invention provides that the device is used within the scope of an optical carbon dioxide sensor for determining the carbon dioxide concentration in the air of a vehicle passenger compartment.

An example embodiment of the present invention provides that the infrared radiation is emitted to a selected side or direction. This makes it possible to focus the radiation in the direction toward the receiver (e.g., a radiation detector), needless irradiation in other directions being avoided or reduced.

DETAILED DESCRIPTION

Figure 1:
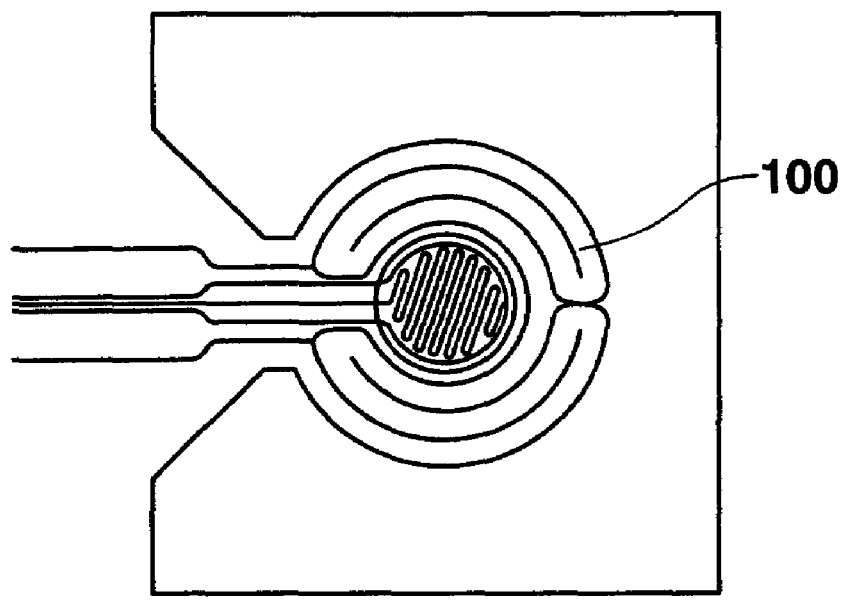
FIG. 1 shows an example embodiment of the heating element of the infrared source.

The use of a micromechanical sensor element or a sensor element manufactured using hybrid technology represents a cost-effective radiation source for a spectroscopic gas sensor or fluid sensor having an irradiation maximum in the desired MIR range. This makes it possible to omit material that absorbs in this wavelength range, such as glass, for example, in the radiation path of the IR source configured in this way.

The power consumption and the overall size of the radiation source are reduced since the predominant portion of the radiation is generated in the required wavelength range. For spectroscopic sensors, the radiation proportion of IR sources (e.g., incandescent lamps) generated in the more short-waved range is dispensed with as undesirable power loss. The yield of the desired infrared radiation is increased by omitting a cover for the radiation source having a material that absorbs in the relevant wavelength range.

A radiation source manufactured using hybrid technology is described below as the first exemplary embodiment.

A heater structure, such as the heater structure of chemical sensor elements, is applied on a ceramic substrate, e.g., aluminum oxide ceramic. For example, a platinum structure is used for this purpose. This platinum structure as the heater structure may generate long-term stable temperatures up to a range of approximately 450° C. (725 K).

According to Wien's displacement law, the maximum of the radiant power of a black-body radiator is reached at a wavelength of approximately 2890/T [μm K], where T indicates the temperature of the radiator. A desired radiation maximum at a wavelength of 4 μm results in a required temperature of 722 K (450° C.); a desired radiation maximum at a wavelength of 4.3 μm results in a required temperature of 672 K (400° C.).

Real radiation sources differ from the ideal for a black-body radiator by their emissivity factor which, depending on the material, deviates to a greater or lesser extent downward from the maximum irradiation of the black-body radiator. This means that the irradiated power of a radiation source is dependent on the absorption factor of the radiator material at the selected temperature. The absorption factor is at the same time the emissivity factor according to Kirchhoff's law. The absorption factor and the emissivity factor show dispersion, i.e., they are temperature-dependent. Metals, in particular bare metals, have emissivity factors at around 10%; in contrast, ceramic materials such as, for example, AlO have emissivity factors close to 90%.

A directional effect of the IR radiation source is established by applying a platinum heater structure (e.g., over the full surface) on one side of an aluminum oxide carrier ceramic and using the opposite (back) side of the carrier ceramic without metallic plating as the irradiation surface. As the directional effect becomes stronger, the more the emissivity factors of the materials used differ. Therefore, it is advantageous to select a metal, such as Pt, which does not oxidize readily, for the metal plating of the heater side since, in the long term, a poorly emitting, bare metallic surface may be ensured even at the required temperatures of up to 450°C. Polishing of this metal surface also has an advantageous effect.

Blackening of the surface or coating the ceramic with a particularly well emitting material likewise has an advantageous effect on the ceramic side used as the irradiation surface. Coatings with ruthenium oxide, a material which is also used in thick film technology for manufacturing resistors, have been shown to be favorable.

In a second example embodiment, the radiation source is configured using a micromechanical element.

Similar to the above-described configuration using hybrid technology, a micromechanical configuration may also be implemented in which a thin diaphragm for thermally insulating the infrared radiation source is created, for example, using micromechanical silicon technology, a Pt heater structure, as a heater coil or a wave-shape structure, for example, being applied on the diaphragm. Comparable to the micromechanical configuration of a chemical sensor or to the micromechanical configuration of an IR detector chip, an emission layer, e.g., the above-described ruthenium oxide, is applied over this heater structure using a dispensing method.

The emission layer has the function of improving the otherwise poor emissivity of silicon and platinum in the infrared range.

The assembly of the micromechanical radiator takes place similar to the assembly of micromechanical sensor elements, in premolded housings, for example, the covers of which are provided with an opening for the emission of the infrared radiation. The directional effect of the infrared radiation may be achieved via the shape and size of the cover opening.

The present invention is described below in conjunction with FIGS. 1 through 4.

Figure 2:
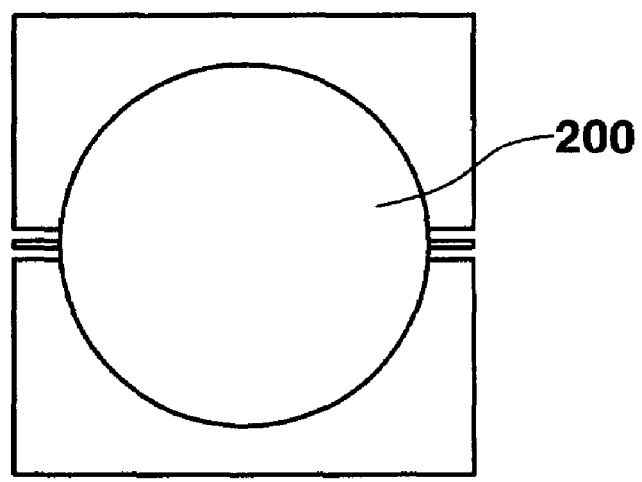
FIG. 2 shows the applied emission layer.
Figure 3:
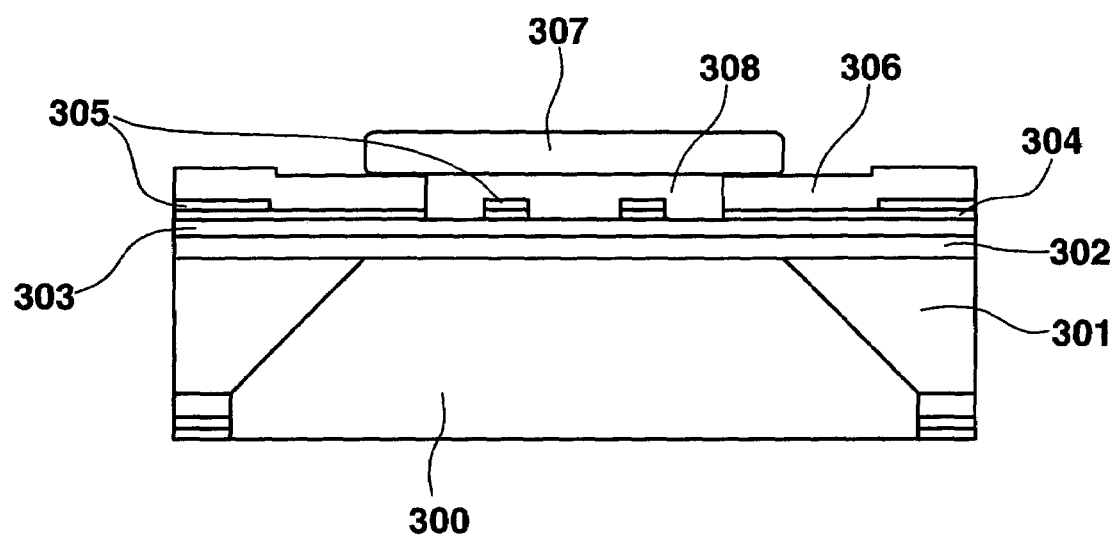
FIG. 3 shows a lateral cross section through the micromechanical infrared source.
Figure 4:
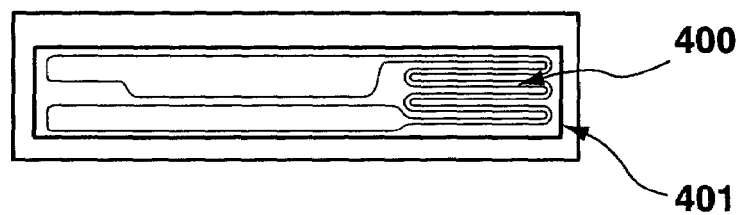
FIG. 4 shows the top view of a further example embodiment of the micromechanical infrared source.

FIGS. 1 through 3 refer to the second example embodiment, and FIG. 4 refers to the first example embodiment.

FIG. 1 shows a wave-shape heater structure 100 which is heated to the required radiator temperature by current flow (generation of ohmic heat). The heater is a platinum structure, as an exemplary embodiment. For a temperature-controlled operation, a second platinum structure may optionally be utilized as a temperature detector (Pt has a positive temperature coefficient, i.e., the specific resistance increases with rising temperature). Also for temperature control, the heater structure itself (the resistance of the heater arises from the ratio (applied voltage)/current) may be utilized for temperature restoration.

FIG. 2 shows emission layer 200 applied on the chip shown in FIG. 1 via a micro-dispensing method.

A lateral cross section through a micromechanical configuration is illustrated in FIG. 3. A thin diaphragm 302 (made of silicon dioxide for example) is applied over a cavern or hollow space 300 which is etched out of substrate material 301. An adhesion-enhancing layer 303 is situated on top of diaphragm 302. This layer 303 provides for the cohesion between the diaphragm 302 and the layers applied on it. This is a protective layer 304, heater structure 305 being applied on it. Four segments of heater structure 305 are shown in cross section in FIG. 3. The two outer segments are slightly wider since the bonding contacts must also be applied to them. Furthermore, passivation layer 306 and emission paste 307 are indicated in FIG. 3. Another protective layer 308 may be situated between emission paste 307 and the heater structure (as in the embodiment according to FIG. 3).

A radiation source according to the first example embodiment is illustrated in FIG. 4. FIG. 4 shows a wave-shape heater structure 400 on a ceramic substrate 401. In one embodiment, it is possible to configure the conductors of the heater structure to be slightly wider and the insulating gaps between the conductors to be narrower.

What is claimed is:

1. A device for generating infrared radiation, comprising:
    at least one heating element, wherein the heating element is a micromechanical, two-dimensional heater structure; and
    at least one radiating element for irradiating the infrared radiation, wherein the heating element has a side facing the radiating element and another side facing away from the radiating element.

2. The device as recited in claim 1, wherein the heating element is applied on the radiating element using hybrid technology, and wherein the radiating element has at least one side facing the heating element and at least one side facing away from the heating element.

3. The device as recited in claim 1, wherein the radiating element is a ceramic substrate.

4. The device as recited in claim 3, wherein the ceramic substrate is an aluminum oxide ceramic.

5. The device as recited in claim 3, wherein the side of the ceramic substrate facing away from the heating element is at least one of: (a) blackened; and (b) coated with a material that emits infrared radiation.

6. The device as recited in claim 5, wherein the material that emits infrared radiation is ruthenium oxide.

7. The device as recited in claim 1, wherein the heater structure is made of platinum.

8. The device as recited in claim 2, wherein the heating element has at least one side facing away from the radiating element, and the side facing away from the radiating element is polished.

9. The device as recited in claim 1, wherein the device is a micromechanical element, and wherein a bottom side of the heating element is applied on a diaphragm, and a top side of the heating element is coated with an emission layer.

10. The device as recited in claim 9, wherein the emission layer is made of ruthenium oxide.

11. The device as recited in claim 9, wherein a hollow space is provided below the side of the diaphragm facing away from the heating element.

12. The device as recited in claim 9, wherein the diaphragm is made using micromechanical silicon technology.

13. The device as recited in claim 9, wherein the device is configured for analyzing gases.

14. The device as recited in claim 13, wherein the device is configured for incorporation in an optical sensor for determining the carbon dioxide concentration in the air of a vehicle passenger compartment.

15. The device as recited in claim 1, wherein the device is configured such that the infrared radiation is emitted substantially to one of a selected side and direction.

* * * * *